United States Patent
Folan (10) Patent No.: US 12,268,589 B2
(45) Date of Patent: Apr. 8, 2025

(54) STENT WITH IMPROVED ANTI-MIGRATION PROPERTIES

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/145,583

(22) Filed: Dec. 22, 2022

(65) Prior Publication Data

US 2023/0130924 A1 Apr. 27, 2023

Related U.S. Application Data

(63) Continuation of application No. 16/950,012, filed on Nov. 17, 2020, now Pat. No. 11,564,787.

(Continued)

(51) Int. Cl.
*A61F 2/04* (2013.01)
*A61F 2/07* (2013.01)
*A61F 2/82* (2013.01)

(52) U.S. Cl.
CPC .................. *A61F 2/04* (2013.01); *A61F 2/07* (2013.01); *A61F 2/82* (2013.01); *A61F 2002/044* (2013.01); *A61F 2230/0095* (2013.01)

(58) Field of Classification Search
CPC ...... A61F 2/04; A61F 2/07; A61F 2/82; A61F 2002/044; A61F 2230/0095; A61F 2250/0039
See application file for complete search history.

(56) References Cited

U.S. PATENT DOCUMENTS

| 5,575,818 A | 11/1996 | Pinchuk |
| 5,741,333 A | 4/1998 | Frid |

(Continued)

FOREIGN PATENT DOCUMENTS

| CA | 3053723 A1 | 9/2018 |
| EP | 0808138 B1 | 10/2005 |

(Continued)

OTHER PUBLICATIONS

International Search Report and Written Opinion dated Mar. 22, 2021 for International Application No. PCT/US2020/060839.

*Primary Examiner* — Dinah Baria
(74) *Attorney, Agent, or Firm* — Seager, Tufte & Wickhem, LLP (57) ABSTRACT

An esophageal stent configured to span a stricture may include a tubular body configured to shift between a delivery configuration and a deployed configuration, the tubular body having a first end and a second end. In the deployed configuration: the tubular body defines a first flange portion, a second flange portion, and a saddle portion extending from the first flange portion to the second flange portion; the tubular body further defining an overall longitudinal length extending from the first end to the second end; the first flange portion has a first outer radial extent, and the second flange portion has a second outer radial extent; the first outer radial extent and the second outer radial extent are greater than an outer radial extent of the saddle portion; and a longitudinal length of the saddle portion is at least 50% of the overall longitudinal length of the tubular body.

18 Claims, 5 Drawing Sheets

Related U.S. Application Data (60) Provisional application No. 62/936,922, filed on Nov. 18, 2019.

(56) References Cited

U.S. PATENT DOCUMENTS

| | | | |
|---|---|---|---|
| 5,846,261 A | 12/1998 | Kotula et al. | |
| 5,891,193 A | 4/1999 | Robinson et al. | |
| 6,264,689 B1 | 7/2001 | Colgan et al. | |
| 6,283,992 B1 | 9/2001 | Hankh et al. | |
| 6,468,303 B1 | 10/2002 | Amplatz et al. | |
| 6,616,675 B1 | 9/2003 | Evard et al. | |
| 6,620,122 B2 | 9/2003 | Stinson et al. | |
| 6,626,936 B2 | 9/2003 | Stinson | |
| 6,663,663 B2 | 12/2003 | Kim et al. | |
| 7,018,401 B1 | 3/2006 | Hyodoh et al. | |
| 7,101,392 B2 | 9/2006 | Heath | |
| 7,115,136 B2 | 10/2006 | Park et al. | |
| 7,311,031 B2 | 12/2007 | McCullagh et al. | |
| 7,462,192 B2 | 12/2008 | Norton et al. | |
| 7,591,845 B2 | 9/2009 | Rhim et al. | |
| 7,670,367 B1 | 3/2010 | Chouinard et al. | |
| 7,763,011 B2 | 7/2010 | Ortiz et al. | |
| 8,114,147 B2 | 2/2012 | Wood et al. | |
| 8,151,682 B2 | 4/2012 | Lilburn et al. | |
| 8,357,193 B2 | 1/2013 | Phan et al. | |
| 8,425,539 B2 | 4/2013 | Binmoeller et al. | |
| 8,454,632 B2 | 6/2013 | Binmoeller et al. | |
| 8,677,874 B2 | 3/2014 | Lilburn et al. | |
| 9,439,790 B2 | 9/2016 | Clerc et al. | |
| 10,076,330 B2 | 9/2018 | Sander et al. | |
| 2007/0123922 A1 | 5/2007 | Cooper et al. | |
| 2008/0109069 A1* | 5/2008 | Coleman | A61F 2/064 623/1.36 |
| 2009/0082803 A1 | 3/2009 | Adams et al. | |
| 2009/0270972 A1 | 10/2009 | Lane | |
| 2011/0125249 A1 | 5/2011 | Jensen et al. | |
| 2013/0012969 A1 | 1/2013 | Shin | |
| 2013/0018215 A1* | 1/2013 | Snider | A61F 2/915 600/1 |
| 2018/0092732 A1 | 4/2018 | Kringle et al. | |
| 2018/0185183 A1 | 7/2018 | Christakis et al. | |
| 2018/0280166 A1 | 10/2018 | Walsh et al. | |
| 2018/0338846 A1 | 11/2018 | Folan et al. | |
| 2019/0099589 A1 | 4/2019 | Walsh et al. | |
| 2019/0167453 A1 | 6/2019 | Colby et al. | |
| 2020/0170776 A1 | 6/2020 | Folan | |

FOREIGN PATENT DOCUMENTS

| | | |
|---|---|---|
| EP | 2322122 A1 | 5/2011 |
| EP | 0957773 B1 | 6/2011 |
| EP | 2543323 A1 | 1/2013 |
| EP | 1558149 B1 | 12/2013 |
| EP | 2754415 B1 | 5/2015 |
| EP | 2177181 B1 | 6/2015 |
| KR | 10-2016-0055433 A | 5/2016 |
| WO | 9601599 A1 | 1/1996 |
| WO | 2005011533 A1 | 2/2005 |
| WO | 2009046126 A1 | 4/2009 |
| WO | 2009140195 A1 | 11/2009 |
| WO | 2013086868 A1 | 6/2013 |
| WO | 2015195893 A1 | 12/2015 |
| WO | 2019097424 A2 | 5/2019 |
| WO | 2022066566 A1 | 3/2022 |

* cited by examiner

STENT WITH IMPROVED ANTI-MIGRATION PROPERTIES

CROSS-REFERENCE TO RELATED APPLICATIONS

This application is a continuation of U.S. application Ser. No. 16/950,012, filed Nov. 17, 2020, which claims the benefit of priority of U.S. Provisional Application No. 62/936,922, filed Nov. 18, 2019, the entire disclosures of which are hereby incorporated by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

Some conditions may cause body lumens (e.g., the esophagus, the bile duct, the trachea, the gastrointestinal tract, the vascular system, etc.) becoming restricted, such as by a stricture formation. As a result, it may be necessary to open the body lumen to permit normal function. Some body lumens may be treated with a self-expanding stent. However, some body lumens are also prone to unintended and/or undesired movement or migration of the stent. Some stents have been designed with a flare on one or both ends with an intent to improve anchoring within the body lumen. However, the flared end(s) can sometimes have undesirable consequences, including perforation of the body lumen and/or stenosis formation. There is an ongoing need to provide alternative endoprostheses or stents as well as alternative methods for manufacturing and using endoprostheses or stents.

SUMMARY

In a first aspect, a stent, such as an esophageal stent, configured to span a stricture may comprise a tubular body configured to shift between a delivery configuration and a deployed configuration, the tubular body having a first end and a second end. In the deployed configuration, the tubular body may define a first flange portion proximate the first end, a second flange portion proximate the second end, and a saddle portion extending from the first flange portion to the second flange portion. In the deployed configuration, the tubular body may further define an overall longitudinal length extending from the first end to the second end. In the deployed configuration, the saddle portion may have an outer radial extent, the first flange portion may have a first outer radial extent, and the second flange portion may have a second outer radial extent. In the deployed configuration, the first outer radial extent may be greater than the outer radial extent of the saddle portion. In the deployed configuration, the second outer radial extent may be greater than the outer radial extent of the saddle portion. In the deployed configuration, a longitudinal length of the saddle portion may be at least 50% of the overall longitudinal length of the tubular body.

In addition or alternatively, in the deployed configuration, the first flange portion may comprise a first flange proximate the first end and a second flange longitudinally spaced apart from the first flange toward the second end.

In addition or alternatively, in the deployed configuration, the second flange may be spaced apart from the first flange about 5 mm to about 10 mm.

In addition or alternatively, in the deployed configuration, the second flange portion may comprise a third flange proximate the second end and a fourth flange longitudinally spaced apart from the third flange toward the first end.

In addition or alternatively, in the deployed configuration, the fourth flange may be spaced apart from the third flange about 5 mm to about 10 mm.

In addition or alternatively, in the deployed configuration, the first flange portion may be configured to resist a first radial inward force, the second flange portion may be configured to resist a second radial inward force, and the saddle portion may be configured to resist a third radial inward force less than the first radial inward force and the second radial inward force.

In addition or alternatively, in the deployed configuration, the first radial inward force may be within 10% of the second radial inward force.

In addition or alternatively, in the deployed configuration, the third radial inward force may be less than 75% of the first radial inward force or the second radial inward force.

In addition or alternatively, in the deployed configuration, the longitudinal length of the saddle portion may be at least 75% of the overall length of the tubular body.

In addition or alternatively, at least a portion of the tubular body may include a cover member.

In addition or alternatively, an esophageal stent configured to span a stricture may comprise a tubular body configured to shift between a delivery configuration and a deployed configuration, the tubular body having a first end and a second end. In the deployed configuration, the tubular body may define a first flange portion proximate the first end, a second flange portion proximate the second end, and a saddle portion extending from the first flange portion to the second flange portion. In the deployed configuration, the tubular body may further define an overall longitudinal length extending from the first end to the second end. In the deployed configuration, the saddle portion may have an outer radial extent, the first flange portion may have a first outer radial extent, and the second flange portion may have a second outer radial extent. In the deployed configuration, the first outer radial extent may be greater than the outer radial extent of the saddle portion. In the deployed configuration, the second outer radial extent may be greater than the outer radial extent of the saddle portion. In the deployed configuration, the saddle portion may include a first radially inward taper extending from the first flange portion toward the second flange portion.

In addition or alternatively, in the deployed configuration, the saddle portion may include a second radially inward taper extending from the second flange portion toward the first flange portion.

In addition or alternatively, in the deployed configuration, the first flange portion may comprise a first flange proximate the first end and a second flange longitudinally spaced apart from the first flange toward the second end.

In addition or alternatively, in the deployed configuration, the second flange may be spaced apart from the first flange about 5 mm to about 10 mm.

In addition or alternatively, in the deployed configuration, the second flange portion may comprise a third flange proximate the second end and a fourth flange longitudinally spaced apart from the third flange toward the first end.

In addition or alternatively, in the deployed configuration, the fourth flange may be spaced apart from the third flange about 5 mm to about 10 mm.

In addition or alternatively, in the deployed configuration, the second outer radial extent may be within 10% of the first outer radial extent.

In addition or alternatively, in the deployed configuration, the second outer radial extent may be within 5% of the first outer radial extent.

In addition or alternatively, at least a portion of the tubular body may include a cover member.

In addition or alternatively, a method of treating a stricture in a body lumen may comprise positioning a stent within the body lumen in a delivery configuration, wherein the stent may be positioned with a saddle portion of the stent spanning the stricture, a first flange portion proximal of the stricture, and a second flange portion distal of the stricture. The method may further comprise shifting the stent from the delivery configuration to a deployed configuration. In the deployed configuration, the first flange portion may have a first outer radial extent greater than an outer radial extent of the saddle portion. In the deployed configuration, the second flange portion may have a second outer radial extent greater than the outer radial extent of the saddle portion. In the deployed configuration, a first flange of the first flange portion and a second flange of the first flange portion longitudinally spaced apart from the first flange may capture a first portion of a wall of the body lumen therebetween to anchor the stent adjacent the stricture. In the deployed configuration, a third flange of the second flange portion and a fourth flange of the second flange portion longitudinally spaced apart from the third flange may capture a second portion of the wall of the body lumen therebetween to anchor the stent adjacent the stricture.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the flange", "the end", "the filament", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

Figure 1:
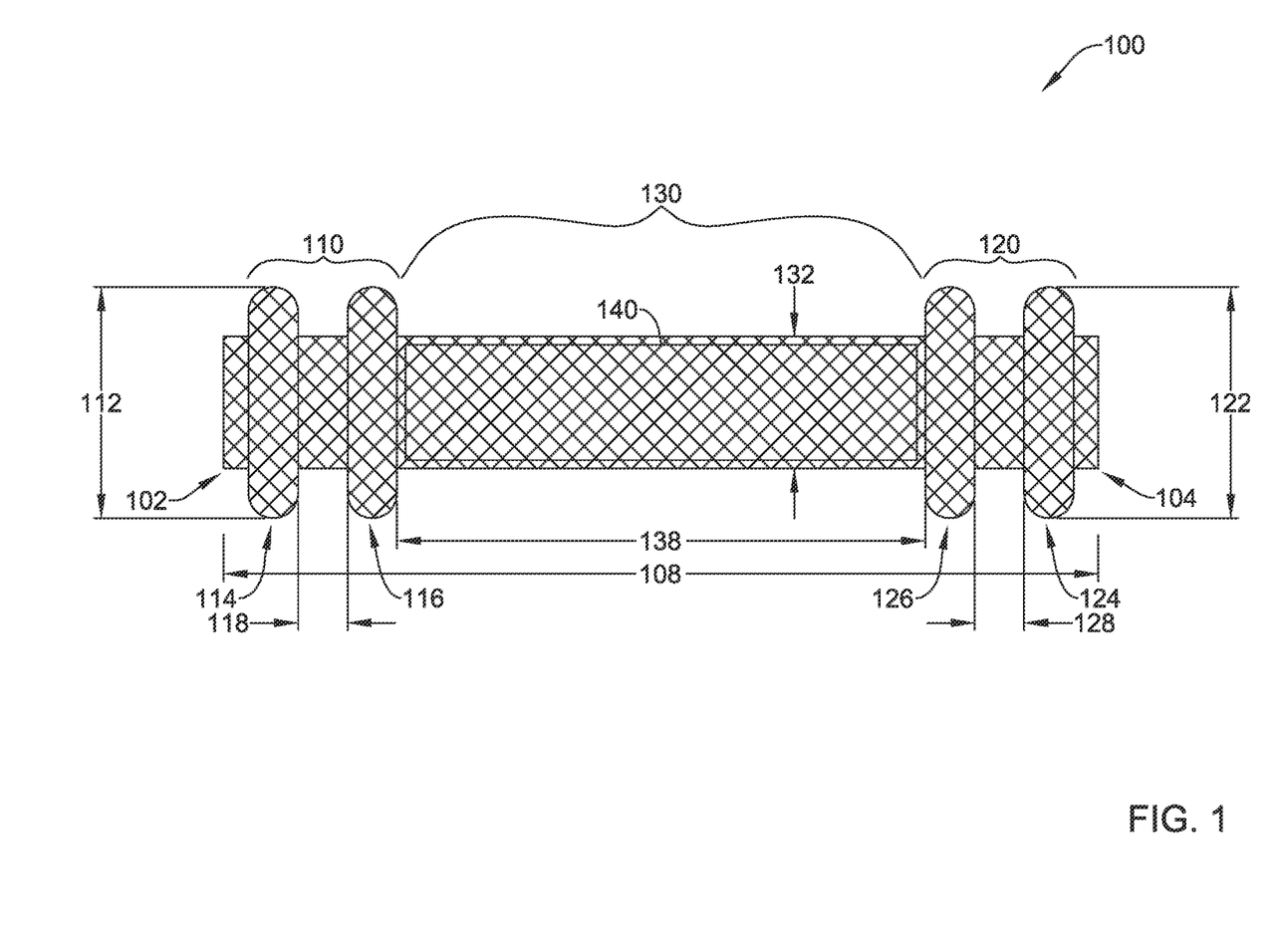
FIG. 1 illustrates aspects of an example stent.

FIG. 1 illustrates an example stent (which term may be used interchangeably with the term "endoprosthesis") comprising a tubular body 100 configured to shift between a delivery configuration (e.g., FIG. 4) and a deployed configuration, the tubular body 100 having a first end 102 and a second end 104. In some embodiments, the delivery configuration may be axially elongated and/or radially collapsed or compressed compared to the deployed configuration. The deployed configuration may be axially shortened and/or radially expanded compared to the delivery configuration.

In some embodiments, the tubular body 100 may comprise an expandable framework. In at least some embodiments, the tubular body 100 and/or the expandable framework may be self-expandable. For example, the tubular body 100 and/or the expandable framework may be formed from a shape memory material. In some embodiments, the tubular body 100 and/or the expandable framework may be mechanically expandable. For example, the tubular body 100 and/or the expandable framework may be expandable using an inflatable balloon, using an actuation member, or other suitable means. During delivery to a treatment site, the tubular body 100 and/or the expandable framework may be disposed within a lumen of a delivery sheath in the delivery configuration. Upon removal from the lumen of the delivery sheath, the tubular body 100 and/or the expandable framework may be shifted to the deployed configuration.

In some embodiments, in the deployed configuration, the tubular body 100 and/or the expandable framework may define a first flange portion 110 proximate the first end 102, a second flange portion 120 proximate the second end 104, and a saddle portion 130 extending from the first flange portion 110 to the second flange portion 120. The saddle portion 130 may be a cylindrical portion having a constant outer diameter along its entire length, for example. The tubular body 100 and/or the expandable framework may define an overall longitudinal length 108 extending from the first end 102 to the second end 104. In some embodiments, a longitudinal length 138 of the saddle portion 130 may be at least 50% of the overall longitudinal length 108 of the tubular body 100. In some embodiments, the longitudinal length 138 of the saddle portion 130 may be at least 75% of the overall longitudinal length 108 of the tubular body 100. The tubular body 100 and/or the expandable framework may define a longitudinally oriented lumen extending therethrough from the first end 102 to the second end 104. In at least some embodiments, the first flange portion 110 and/or the second flange portion 120 may be coaxial with the saddle portion 130. In at least some embodiments, the first flange portion 110 and the second flange portion 120 may be monolithically formed with the saddle portion 130 as a single unitary structure (e.g., the plurality of interwoven filaments forming the saddle portion 130 extend throughout the first flange portion 110 to form the first flange portion 110 and/or extend throughout the second flange portion 120 to form the second flange portion 120). In some embodiments, at least a portion of the tubular body 100 and/or the expandable framework extends proximal of the first flange portion 110. In some embodiments, at least a portion of the tubular body 100 and/or the expandable framework extends distal of the second flange portion 120.

In some embodiments, in the deployed configuration, the saddle portion 130 may have an outer radial extent 132, the first flange portion 110 may have a first outer radial extent 112, and the second flange portion 120 may have a second outer radial extent 122. In some embodiments, the first outer radial extent 112 may be greater than the outer radial extent 132 of the saddle portion 130. In some embodiments, the second outer radial extent 122 may be greater than the outer radial extent 132 of the saddle portion 130. In some embodiments, the second outer radial extent 122 may be within about 25% of the first outer radial extent 112. In some embodiments, the second outer radial extent 122 may be within about 10% of the first outer radial extent 112. In some embodiments, the second outer radial extent 122 may be within about 5% of the first outer radial extent 112. In some embodiments, the second outer radial extent 122 may be equal to the first outer radial extent 112. In some embodiments, the outer radial extent 132 of the saddle portion 130 may be about 10 mm (millimeters) to about 30 mm, about 14 mm to about 25 mm, about 16 mm to about 22 mm, or another suitable range. In some embodiments, the first outer radial extent 112 and/or the second outer radial extent 122 may be about 20 mm to about 40 mm, about 24 mm to about 35 mm, about 26 mm to about 32 mm, or another suitable range. In some embodiments, an outer radial extent of the tubular body 100 and/or the expandable framework at the first end 102 may be substantially equal to an outer radial extent of the tubular body 100 and/or the expandable framework at the second end 104. Other configurations are also contemplated.

In some embodiments, in the deployed configuration, the first flange portion 110 may comprise multiple spaced apart flanges, such as a first flange 114 proximate the first end 102 and a second flange 116 longitudinally spaced apart from the first flange 114 toward the second end 104. The first flange 114 and the second flange 116 may be oriented generally transverse to a central longitudinal axis of the tubular body 100. In some embodiments, the second flange 116 may be longitudinally spaced apart from the first flange 114 about 2 mm to about 20 mm, about 4 mm to about 15 mm, about 5 mm to about 10 mm, or another suitable range. In some embodiments, the first flange 114 and/or the second flange 116 may have an axial thickness of about 1 mm to about 7 mm, about 2 mm to about 6 mm, about 3 mm to about 5 mm, or another suitable range. Other configurations are also contemplated.

In some embodiments, in the deployed configuration, the second flange portion 120 may comprise multiple spaced apart flanges, such as a third flange 124 proximate the second end 104 and a fourth flange 126 longitudinally spaced apart from the third flange 124 toward the first end 102. The third flange 124 and the fourth flange 126 may be oriented generally transverse to the central longitudinal axis of the tubular body 100. In some embodiments, the fourth flange 126 may be longitudinally spaced apart from the third flange 124 about 2 mm to about 20 mm, about 4 mm to about 15 mm, about 5 mm to about 10 mm, or another suitable range. In some embodiments, the third flange 124 and/or the fourth flange 126 may have an axial thickness of about 1 mm to about 7 mm, about 2 mm to about 6 mm, about 3 mm to about 5 mm, or another suitable range. Other configurations are also contemplated.

In some embodiments, in the deployed configuration, the first flange portion 110 (and/or the first flange 114 and the second flange 116) may be configured to resist collapsing radially inward under a first radial inward force, the second flange portion 120 (and/or the third flange 124 and the fourth flange 126) may be configured to resist collapsing radially inward under a second radial inward force, and the saddle portion 130 may be configured to resist collapsing radially inward under a third radial inward force less than the first radial inward force and the second radial inward force. In some embodiments, the first radial inward force may be within about 25% of the second radial inward force. In some embodiments, the first radial inward force may be within about 10% of the second radial inward force. In some embodiments, the first radial inward force may be within about 5% of the second radial inward force. In some embodiments, the third radial inward force may be less than about 75% of the first radial inward force and/or the second radial inward force. In some embodiments, the third radial inward force may be less than about 50% of the first radial inward force and/or the second radial inward force. In some embodiments, the first radial inward force and/or the second radial inward force may be about 300% to about 500% greater than the third radial inward force. Other configurations are also contemplated.

In some embodiments, in the deployed configuration, the tubular body 100 may define an outer surface that may extend, sequentially, from the first end: longitudinally, radially outward, curve back on itself to radially inward, longitudinally, radially outward, curve back on itself to radially inward, longitudinally, radially outward, curve back on itself to radially inward, longitudinally, radially outward, curve back on itself to radially inward, and longitudinally, to the second end. In other words, each flange may include first and second radially extending wall portions longitudinally spaced apart from one another with an apical curved region spanning therebetween at the outer extent of the flange, with a first radially extending wall portion extend radially outward from the central longitudinal axis to an outer extent of the flange and the second radially extending wall portion extending radially inward from the outer extent of the flange toward the central longitudinal axis. Other configurations are also contemplated.

In some embodiments, the tubular body 100 may be formed from a plurality of filaments or wires that may be woven, braided, wound, knitted, and combinations thereof, around a central longitudinal axis to form the tubular body 100. The tubular body 100 may include multiple filaments or wires of a metal material, such as nitinol or nitinol-containing material, or other nickel-titanium alloy, for example. In some instances, the filaments or wires may have a diameter of about 0.011 inches (0.2794 mm), for example. The number and the diameters of the filaments or wires, which may be the same or different, are not limiting, and other numbers and other diameters of filaments or wires may suitably be used. Desirably, an even number of filaments or wires may be used, for example, from about 2 to about 50 filaments or wires, about 6 to about 40 filaments or wires, about 10 to about 36 filaments or wires, etc.

Desirably, the filaments or wires are made from any suitable implantable biocompatible material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Filaments or wires made from polymeric materials may also include radiopaque materials, such as metallic-based powders, particulates or pastes which may be incorporated into the polymeric material. For example, the radiopaque material may be blended with the polymer composition from which the polymeric filaments or wires are formed, and subsequently fashioned into the tubular body 100 as described herein. Alternatively, the radiopaque material may be applied to the surface of the metal or polymer filaments or wires of the tubular body 100. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The tubular body 100 may be selectively made radiopaque at desired areas along the filaments or wires or may be fully radiopaque.

In some instances, the filaments or wires may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the filaments or wires based on overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The filaments or wires may be made from nitinol, or composite filaments or wires having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof. Additional and/or other materials suitable for use in the tubular body 100 are described below.

In some embodiments, the tubular body 100 may optionally include a polymeric cover 140 disposed on at least a portion of the tubular body 100 and/or the expandable framework. In some embodiments, the polymeric cover 140 may be disposed on the saddle portion 130, as shown in FIG. 1 for example. In some embodiments, the polymeric cover 140 may additionally or alternatively be disposed on the first flange portion 110 and/or the second flange portion 120. In some embodiments, the polymeric cover 140 may be disposed on the first flange portion 110, the second flange portion 120, and the saddle portion 130. In some embodiments, the polymeric cover 140 may be disposed on and/or along an outer surface of the tubular body 100 and/or the expandable framework. In some embodiments, the tubular body 100 and/or the expandable framework may be embedded in the polymeric cover 140. In some embodiments, the polymeric cover 140 may be disposed on and/or along an inner surface of the tubular body 100 and/or the expandable framework. In some embodiments, the polymeric cover 140 may be fixedly or releasably secured to, bonded to, or otherwise attached to the tubular body 100 and/or the expandable framework. In some embodiments, the polymeric cover 140 may be impermeable to fluids, debris, medical instruments, etc. Some suitable but non-limiting materials for the polymeric cover 140 are described below.

Figure 2:
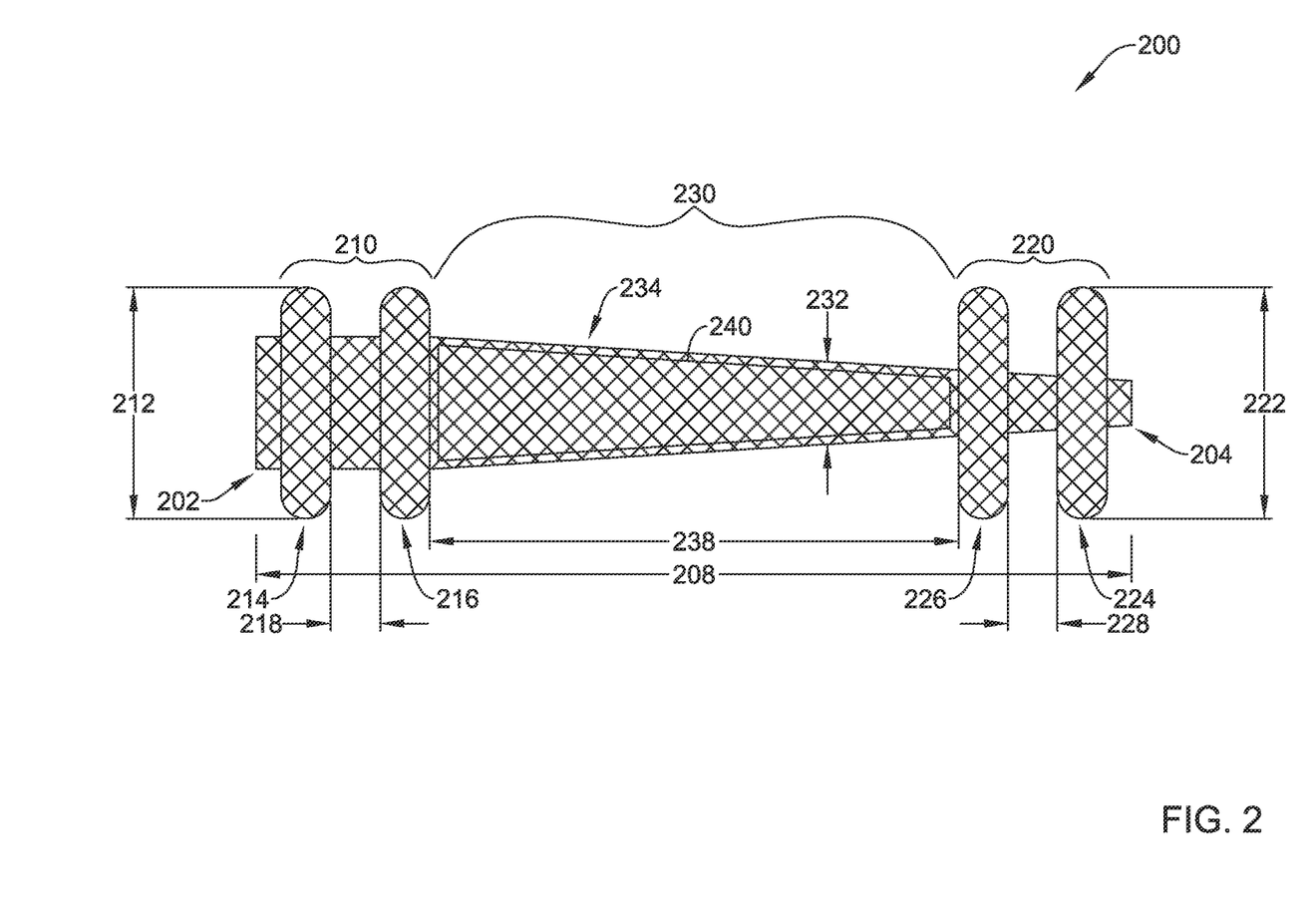
FIG. 2 illustrates aspects of an example stent.

FIG. 2 illustrates an example stent (which term may be used interchangeably with the term "endoprosthesis") comprising a tubular body 200 configured to shift between a delivery configuration (e.g., FIG. 4) and a deployed configuration, the tubular body 200 having a first end 202 and a second end 204. In some embodiments, the delivery configuration may be axially elongated and/or radially collapsed or compressed compared to the deployed configuration. The deployed configuration may be axially shortened and/or radially expanded compared to the delivery configuration. The tubular body 200 may be constructed and/or may function similar to the tubular body 100 described herein, except for any specific differences noted.

In some embodiments, the tubular body 200 may comprise an expandable framework. In at least some embodiments, the tubular body 200 and/or the expandable framework may be self-expandable. For example, the tubular body 200 and/or the expandable framework may be formed from a shape memory material. In some embodiments, the tubular body 200 and/or the expandable framework may be mechanically expandable. For example, the tubular body 200 and/or the expandable framework may be expandable using an inflatable balloon, using an actuation member, or other suitable means. During delivery to a treatment site, the tubular body 200 and/or the expandable framework may be disposed within a lumen of a delivery sheath in the delivery configuration. Upon removal from the lumen of the delivery sheath, the tubular body 200 and/or the expandable framework may be shifted to the deployed configuration.

In some embodiments, in the deployed configuration, the tubular body 200 and/or the expandable framework may define a first flange portion 210 proximate the first end 202, a second flange portion 220 proximate the second end 204, and a saddle portion 230 extending from the first flange portion 210 to the second flange portion 220. The tubular body 200 and/or the expandable framework may define an overall longitudinal length 208 extending from the first end 202 to the second end 204. In some embodiments, a longitudinal length 238 of the saddle portion 230 may be at least 50% of the overall longitudinal length 208 of the tubular body 200. In some embodiments, the longitudinal length 238 of the saddle portion 230 may be at least 75% of the overall longitudinal length 208 of the tubular body 200. The tubular body 200 and/or the expandable framework may define a longitudinally oriented lumen extending therethrough from the first end 202 to the second end 204. In at least some embodiments, the first flange portion 210 and/or the second flange portion 220 may be coaxial with the saddle portion 230. In at least some embodiments, the first flange portion 210 and the second flange portion 220 may be monolithically formed with the saddle portion 230 as a single unitary structure. In some embodiments, at least a portion of the tubular body 200 and/or the expandable framework extends proximal of the first flange portion 210. In some embodiments, at least a portion of the tubular body 200 and/or the expandable framework extends distal of the second flange portion 220.

In some embodiments, in the deployed configuration, the saddle portion 230 may have an outer radial extent 232, the first flange portion 210 may have a first outer radial extent 212, and the second flange portion 220 may have a second outer radial extent 222. In some embodiments, the first outer radial extent 212 may be greater than the outer radial extent 232 of the saddle portion 230. In some embodiments, the second outer radial extent 222 may be greater than the outer radial extent 232 of the saddle portion 230. In some embodiments, the second outer radial extent 222 may be within about 25% of the first outer radial extent 212. In some embodiments, the second outer radial extent 222 may be within about 10% of the first outer radial extent 212. In some embodiments, the second outer radial extent 222 may be within about 5% of the first outer radial extent 212. In some embodiments, the second outer radial extent 222 may be equal to the first outer radial extent 212. In some embodiments, the outer radial extent 232 of the saddle portion 230 may be about 10 mm (millimeters) to about 30 mm, about 14 mm to about 25 mm, about 16 mm to about 22 mm, or another suitable range. In some embodiments, the first outer radial extent 212 and/or the second outer radial extent 222 may be about 20 mm to about 40 mm, about 24 mm to about 35 mm, about 26 mm to about 32 mm, or another suitable range. Other configurations are also contemplated.

In some embodiments, in the deployed configuration, the saddle portion 230 may be conically shaped, tapering from the first flange portion 210 to the second flange portion 220. For instance, the saddle portion 230 of the tubular body 200 may include a first radially inward taper 234 extending from the first flange portion 210 toward the second flange portion 220. In some embodiments, the first radially inward taper 234 may extend from the first flange portion 210 to the second flange portion 220. In some embodiments, the first radially inward taper 234 may extend past the second flange portion 220 toward and/or to the second end 204. In some embodiments, an outer radial extent of the tubular body 200 and/or the expandable framework at the second end 204 may be substantially less than an outer radial extent of the tubular body 200 and/or the expandable framework at the first end 202. In some embodiments, the outer radial extent of the tubular body 200 and/or the expandable framework at the second end 204 may be about 25% to about 50% less than the outer radial extent of the tubular body 200 and/or the expandable framework at the first end 202. Other configurations are also contemplated.

In some embodiments, in the deployed configuration, the first flange portion 210 may comprise multiple spaced apart flanges, such as a first flange 214 proximate the first end 202 and a second flange 216 longitudinally spaced apart from the first flange 214 toward the second end 204. The first flange 214 and the second flange 216 may be oriented generally transverse to a central longitudinal axis of the tubular body 200. In some embodiments, the second flange 216 may be longitudinally spaced apart from the first flange 214 about 2 mm to about 20 mm, about 4 mm to about 15 mm, about 5 mm to about 10 mm, or another suitable range. In some embodiments, the first flange 214 and/or the second flange 216 may have an axial thickness of about 1 mm to about 7 mm, about 2 mm to about 6 mm, about 3 mm to about 5 mm, or another suitable range. Other configurations are also contemplated.

In some embodiments, in the deployed configuration, the second flange portion 220 may comprise multiple spaced apart flanges, such as a third flange 224 proximate the second end 204 and a fourth flange 226 longitudinally spaced apart from the third flange 224 toward the first end 202. The third flange 224 and the fourth flange 226 may be oriented generally transverse to the central longitudinal axis of the tubular body 200. In some embodiments, the fourth flange 226 may be longitudinally spaced apart from the third flange 224 about 2 mm to about 20 mm, about 4 mm to about 15 mm, about 5 mm to about 10 mm, or another suitable range. In some embodiments, the third flange 224 and/or the fourth flange 226 may have an axial thickness of about 1 mm to about 7 mm, about 2 mm to about 6 mm, about 3 mm to about 5 mm, or another suitable range. Other configurations are also contemplated. In at least some embodiments, the second flange portion 220, the third flange 224, and/or the fourth flange 226 may extend a greater distance radially outward from the saddle portion 230 than the first flange portion 210, the first flange 214, and/or the second flange 216.

In some embodiments, in the deployed configuration, the first flange portion 210 (and/or the first flange 214 and the second flange 216) may be configured to resist collapsing radially inward under a first radial inward force, the second flange portion 220 (and/or the third flange 224 and the fourth flange 226) may be configured to resist collapsing radially inward under a second radial inward force, and the saddle portion 230 may be configured to resist collapsing radially inward under a third radial inward force less than the first radial inward force and the second radial inward force. In some embodiments, the first radial inward force may be within about 25% of the second radial inward force. In some embodiments, the first radial inward force may be within about 10% of the second radial inward force. In some embodiments, the first radial inward force may be within about 5% of the second radial inward force. In some embodiments, the third radial inward force may be less than about 75% of the first radial inward force and/or the second radial inward force. In some embodiments, the third radial inward force may be less than about 50% of the first radial inward force and/or the second radial inward force. In some embodiments, the first radial inward force and/or the second radial inward force may be about 300% to about 500% greater than the third radial inward force. Other configurations are also contemplated.

In some embodiments, in the deployed configuration, the tubular body 200 may define an outer surface that may extend, sequentially, from the first end: longitudinally, radially outward, curve back on itself to radially inward, longitudinally, radially outward, curve back on itself to radially inward, longitudinally along a radially inward taper, radially outward, curve back on itself to radially inward, longitudinally (and in at least some embodiments, longitudinally along a radially inward taper), radially outward, curve back on itself to radially inward, and longitudinally (and in at least some embodiments, longitudinally along a radially inward taper), to the second end. In other words, each flange may include first and second radially extending wall portions longitudinally spaced apart from one another with an apical curved region spanning therebetween at the outer extent of the flange, with a first radially extending wall portion extend radially outward from the central longitudinal axis to an outer extent of the flange and the second radially extending wall portion extending radially inward from the outer extent of the flange toward the central longitudinal axis. Other configurations are also contemplated.

In some embodiments, the tubular body 200 may be formed from a plurality of filaments or wires that may be woven, braided, wound, knitted, and combinations thereof, around a central longitudinal axis to form the tubular body 200. The tubular body 200 may include multiple filaments or wires of a metal material, such as nitinol or nitinol-containing material, or other nickel-titanium alloy, for example. In some instances, the filaments or wires may have a diameter of about 0.011 inches (0.2794 mm), for example. The number and the diameters of the filaments or wires, which may be the same or different, are not limiting, and other numbers and other diameters of filaments or wires may suitably be used. Desirably, an even number of filaments or wires may be used, for example, from about 2 to about 50 filaments or wires, about 6 to about 40 filaments or wires, about 10 to about 36 filaments or wires, etc.

Desirably, the filaments or wires are made from any suitable implantable biocompatible material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Filaments or wires made from polymeric materials may also include radiopaque materials, such as metallic-based powders, particulates or pastes which may be incorporated into the polymeric material. For example, the radiopaque material may be blended with the polymer composition from which the polymeric filaments or wires are formed, and subsequently fashioned into the tubular body 200 as described herein. Alternatively, the radiopaque material may be applied to the surface of the metal or polymer filaments or wires of the tubular body 200. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The tubular body 200 may be selectively made radiopaque at desired areas along the filaments or wires or may be fully radiopaque.

In some instances, the filaments or wires may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the filaments or wires based on overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The filaments or wires may be made from nitinol, or composite filaments or wires having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof. Additional and/or other materials suitable for use in the tubular body 200 are described below.

In some embodiments, the tubular body 200 and/or the expandable framework may optionally include a polymeric cover 240 disposed on at least a portion of the tubular body 200 and/or the expandable framework. In some embodiments, the polymeric cover 240 may be disposed on the saddle portion 230, as shown in FIG. 2 for example. In some embodiments, the polymeric cover 240 may additionally or alternatively be disposed on the first flange portion 210 and/or the second flange portion 220. In some embodiments, the polymeric cover 240 may be disposed on the first flange portion 210, the second flange portion 220, and the saddle portion 230. In some embodiments, the polymeric cover 240 may be disposed on and/or along an outer surface of the tubular body 200 and/or the expandable framework. In some embodiments, the tubular body 200 and/or the expandable framework may be embedded in the polymeric cover 240. In some embodiments, the polymeric cover 240 may be disposed on and/or along an inner surface of the tubular body 200 and/or the expandable framework. In some embodiments, the polymeric cover 240 may be fixedly or releasably secured to, bonded to, or otherwise attached to the tubular body 200 and/or the expandable framework. In some embodiments, the polymeric cover 240 may be impermeable to fluids, debris, medical instruments, etc. Some suitable but non-limiting materials for the polymeric cover 240 are described below.

Figure 3:
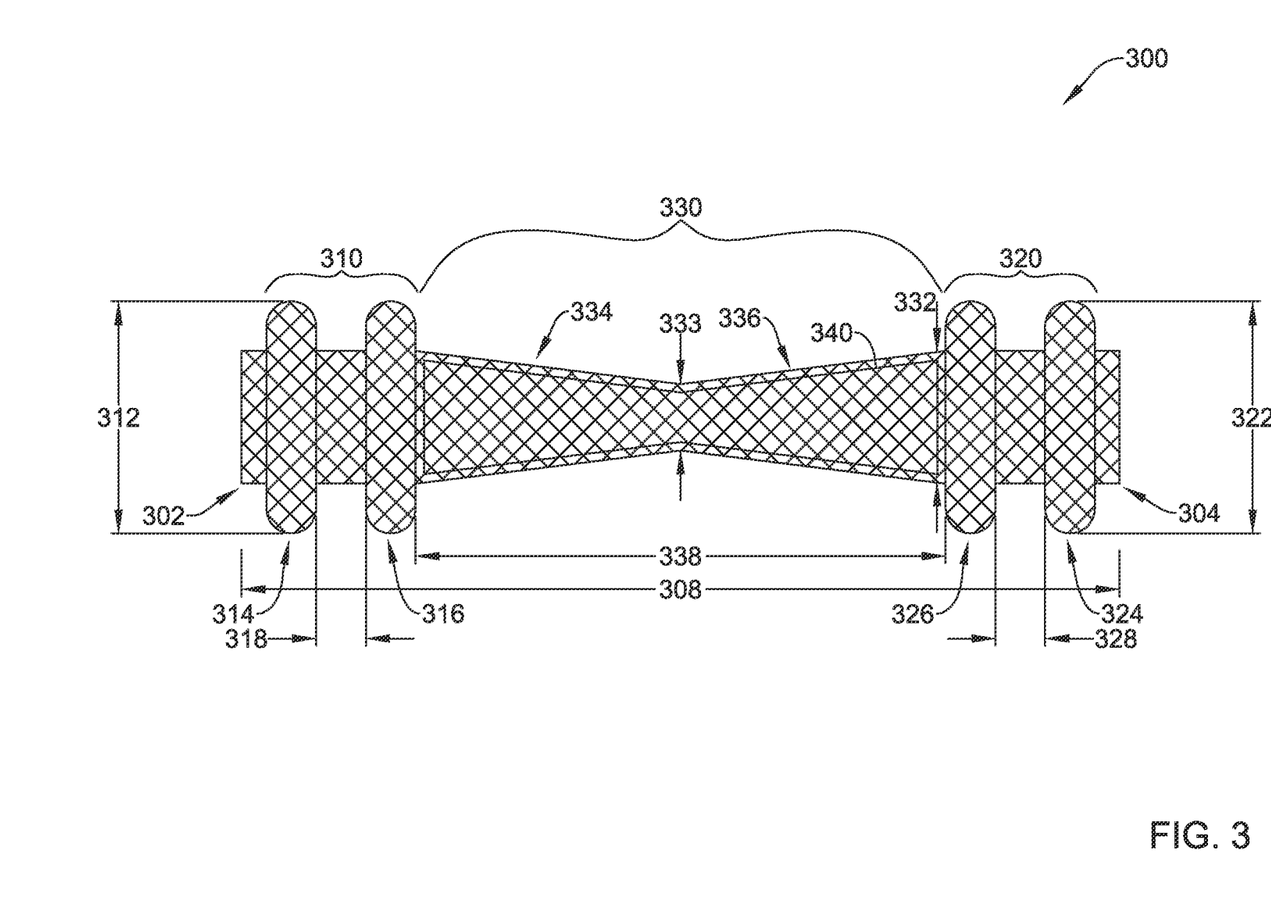
FIG. 3 illustrates aspects of an example stent.

FIG. 3 illustrates an example stent (which term may be used interchangeably with the term "endoprosthesis") comprising a tubular body 300 configured to shift between a delivery configuration (e.g., FIG. 4) and a deployed configuration, the tubular body 300 having a first end 302 and a second end 304. In some embodiments, the delivery configuration may be axially elongated and/or radially collapsed or compressed compared to the deployed configuration. The deployed configuration may be axially shortened and/or radially expanded compared to the delivery configuration. The tubular body 300 may be constructed and/or may function similar to the tubular body 100/200 described herein, except for any specific differences noted.

In some embodiments, the tubular body 300 may comprise an expandable framework. In at least some embodiments, the tubular body 300 and/or the expandable framework may be self-expandable. For example, the tubular body 300 and/or the expandable framework may be formed from a shape memory material. In some embodiments, the tubular body 300 and/or the expandable framework may be mechanically expandable. For example, the tubular body 300 and/or the expandable framework may be expandable using an inflatable balloon, using an actuation member, or other suitable means. During delivery to a treatment site, the tubular body 300 and/or the expandable framework may be disposed within a lumen of a delivery sheath in the delivery configuration. Upon removal from the lumen of the delivery sheath, the tubular body 300 and/or the expandable framework may be shifted to the deployed configuration.

In some embodiments, in the deployed configuration, the tubular body 300 and/or the expandable framework may define a first flange portion 310 proximate the first end 302, a second flange portion 320 proximate the second end 304, and a saddle portion 330 extending from the first flange portion 310 to the second flange portion 320. The tubular body 300 and/or the expandable framework may define an overall longitudinal length 308 extending from the first end 302 to the second end 304. In some embodiments, a longitudinal length 338 of the saddle portion 330 may be at least 50% of the overall longitudinal length 308 of the tubular body 300. In some embodiments, the longitudinal length 338 of the saddle portion 330 may be at least 75% of the overall longitudinal length 308 of the tubular body 300. The tubular body 300 and/or the expandable framework may define a longitudinally oriented lumen extending therethrough from the first end 302 to the second end 304. In at least some embodiments, the first flange portion 310 and/or the second flange portion 320 may be coaxial with the saddle portion 330. In at least some embodiments, the first flange portion 310 and the second flange portion 320 may be monolithically formed with the saddle portion 330 as a single unitary structure. In some embodiments, at least a portion of the tubular body 300 and/or the expandable framework extends proximal of the first flange portion 310. In some embodiments, at least a portion of the tubular body 300 and/or the expandable framework extends distal of the second flange portion 320.

In some embodiments, in the deployed configuration, the saddle portion 330 may have an outer radial extent 332, the first flange portion 310 may have a first outer radial extent 312, and the second flange portion 320 may have a second outer radial extent 322. In some embodiments, the first outer radial extent 312 may be greater than the outer radial extent 332 of the saddle portion 330. In some embodiments, the second outer radial extent 322 may be greater than the outer radial extent 332 of the saddle portion 330. In some embodiments, the second outer radial extent 322 may be within about 25% of the first outer radial extent 312. In some embodiments, the second outer radial extent 322 may be within about 10% of the first outer radial extent 312. In some embodiments, the second outer radial extent 322 may be within about 5% of the first outer radial extent 312. In some embodiments, the second outer radial extent 322 may be equal to the first outer radial extent 312. In some embodiments, the outer radial extent 332 of the saddle portion 330 may be about 10 mm (millimeters) to about 30 mm, about 14 mm to about 25 mm, about 16 mm to about 22 mm, or another suitable range. In some embodiments, the first outer radial extent 312 and/or the second outer radial extent 322 may be about 20 mm to about 40 mm, about 24 mm to about 35 mm, about 26 mm to about 32 mm, or another suitable range. In some embodiments, an outer radial extent of the tubular body 300 and/or the expandable framework at the first end 302 may be substantially equal to an outer radial extent of the tubular body 300 and/or the expandable framework at the second end 304. Other configurations are also contemplated.

In some embodiments, in the deployed configuration, the saddle portion 330 may be hourglass shaped, tapering from each of the first flange portion 310 and the second flange portion 320 to a necked down central region. For instance, the saddle portion 330 of the tubular body 300 may include a first radially inward taper 334 extending from the first flange portion 310 toward the second flange portion 320. In some embodiments, the saddle portion 330 of the tubular body 300 may include a second radially inward taper 336 extending from the second flange portion 320 toward the first flange portion 310. In some embodiments, the first radially inward taper 334 and the second radially inward taper 336 may converge and/or meet at a reduced diameter neck region 333 of the saddle portion 330 disposed between the first flange portion 310 and the second flange portion 320. In some embodiments, the reduced diameter neck region 333 may include a constant diameter section extending along a portion of the longitudinal length 338 of the saddle portion 330 between the first radially inward taper 334 and the second radially inward taper 336. In some embodiments, the reduced diameter neck region 333 of the saddle portion 330 may be about 25% to about 50% less than the outer radial extent 332 of the saddle portion 330 at and/or adjacent to the first flange portion 310 and/or the second flange portion 320. Other configurations are also contemplated.

In some embodiments, in the deployed configuration, the first flange portion 310 may comprise multiple spaced apart flanges, such as a first flange 314 proximate the first end 302 and a second flange 316 longitudinally spaced apart from the first flange 314 toward the second end 304. The first flange 314 and the second flange 316 may be oriented generally transverse to a central longitudinal axis of the tubular body 300. In some embodiments, the second flange 316 may be longitudinally spaced apart from the first flange 314 about 2 mm to about 20 mm, about 4 mm to about 15 mm, about 5 mm to about 10 mm, or another suitable range. In some embodiments, the first flange 314 and/or the second flange 316 may have an axial thickness of about 1 mm to about 7 mm, about 2 mm to about 6 mm, about 3 mm to about 5 mm, or another suitable range. Other configurations are also contemplated.

In some embodiments, in the deployed configuration, the second flange portion 320 may comprise multiple spaced apart flanges, such as a third flange 324 proximate the second end 304 and a fourth flange 326 longitudinally spaced apart from the third flange 324 toward the first end 302. The third flange 324 and the fourth flange 326 may be oriented generally transverse to the central longitudinal axis of the tubular body 300. In some embodiments, the fourth flange 326 may be longitudinally spaced apart from the third flange 324 about 2 mm to about 20 mm, about 4 mm to about 15 mm, about 5 mm to about 10 mm, or another suitable range. In some embodiments, the third flange 324 and/or the fourth flange 326 may have an axial thickness of about 1 mm to about 7 mm, about 2 mm to about 6 mm, about 3 mm to about 5 mm, or another suitable range. Other configurations are also contemplated.

In some embodiments, in the deployed configuration, the first flange portion 310 (and/or the first flange 314 and the second flange 316) may be configured to resist collapsing radially inward under a first radial inward force, the second flange portion 320 (and/or the third flange 324 and the fourth flange 326) may be configured to resist collapsing radially inward under a second radial inward force, and the saddle portion 330 may be configured to resist collapsing radially inward under a third radial inward force less than the first radial inward force and the second radial inward force. In some embodiments, the first radial inward force may be within about 25% of the second radial inward force. In some embodiments, the first radial inward force may be within about 10% of the second radial inward force. In some embodiments, the first radial inward force may be within about 5% of the second radial inward force. In some embodiments, the third radial inward force may be less than about 75% of the first radial inward force and/or the second radial inward force. In some embodiments, the third radial inward force may be less than about 50% of the first radial inward force and/or the second radial inward force. In some embodiments, the first radial inward force and/or the second radial inward force may be about 300% to about 500% greater than the third radial inward force. Other configurations are also contemplated.

In some embodiments, in the deployed configuration, the tubular body 200 may define an outer surface that may extend, sequentially, from the first end: longitudinally, radially outward, curve back on itself to radially inward, longitudinally, radially outward, curve back on itself to radially inward, longitudinally along a radially inward taper, longitudinally along a radially outward taper, radially outward, curve back on itself to radially inward, longitudinally, radially outward, curve back on itself to radially inward, and longitudinally, to the second end. In other words, each flange may include first and second radially extending wall portions longitudinally spaced apart from one another with an apical curved region spanning therebetween at the outer extent of the flange, with a first radially extending wall portion extend radially outward from the central longitudinal axis to an outer extent of the flange and the second radially extending wall portion extending radially inward from the outer extent of the flange toward the central longitudinal axis. Other configurations are also contemplated.

In some embodiments, the tubular body 300 may be formed from a plurality of filaments or wires that may be woven, braided, wound, knitted, and combinations thereof, around a central longitudinal axis to form the tubular body 300. The tubular body 300 may include multiple filaments or wires of a metal material, such as nitinol or nitinol-containing material, or other nickel-titanium alloy, for example. In some instances, the filaments or wires may have a diameter of about 0.011 inches (0.2794 mm), for example. The number and the diameters of the filaments or wires, which may be the same or different, are not limiting, and other numbers and other diameters of filaments or wires may suitably be used. Desirably, an even number of filaments or wires may be used, for example, from about 2 to about 50 filaments or wires, about 6 to about 40 filaments or wires, about 10 to about 36 filaments or wires, etc.

Desirably, the filaments or wires are made from any suitable implantable biocompatible material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Filaments or wires made from polymeric materials may also include radiopaque materials, such as metallic-based powders, particulates or pastes which may be incorporated into the polymeric material. For example, the radiopaque material may be blended with the polymer composition from which the polymeric filaments or wires are formed, and subsequently fashioned into the tubular body 300 as described herein. Alternatively, the radiopaque material may be applied to the surface of the metal or polymer filaments or wires of the tubular body 300. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The tubular body 300 may be selectively made radiopaque at desired areas along the filaments or wires or may be fully radiopaque.

In some instances, the filaments or wires may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the filaments or wires based on overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The filaments or wires may be made from nitinol, or composite filaments or wires having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof. Additional and/or other materials suitable for use in the tubular body 300 are described below.

In some embodiments, the tubular body 300 and/or the expandable framework may optionally include a polymeric cover 340 disposed on at least a portion of the tubular body 300 and/or the expandable framework. In some embodiments, the polymeric cover 340 may be disposed on the saddle portion 330, as shown in FIG. 3 for example. In some embodiments, the polymeric cover 340 may additionally or alternatively be disposed on the first flange portion 310 and/or the second flange portion 320. In some embodiments, the polymeric cover 340 may be disposed on the first flange portion 310, the second flange portion 320, and the saddle portion 330. In some embodiments, the polymeric cover 340 may be disposed on and/or along an outer surface of the tubular body 300 and/or the expandable framework. In some embodiments, the tubular body 300 and/or the expandable framework may be embedded in the polymeric cover 340. In some embodiments, the polymeric cover 340 may be disposed on and/or along an inner surface of the tubular body 300 and/or the expandable framework. In some embodiments, the polymeric cover 340 may be fixedly or releasably secured to, bonded to, or otherwise attached to the tubular body 300 and/or the expandable framework. In some embodiments, the polymeric cover 340 may be impermeable to fluids, debris, medical instruments, etc. Some suitable but non-limiting materials for the polymeric cover 340 are described below.

Figure 4:
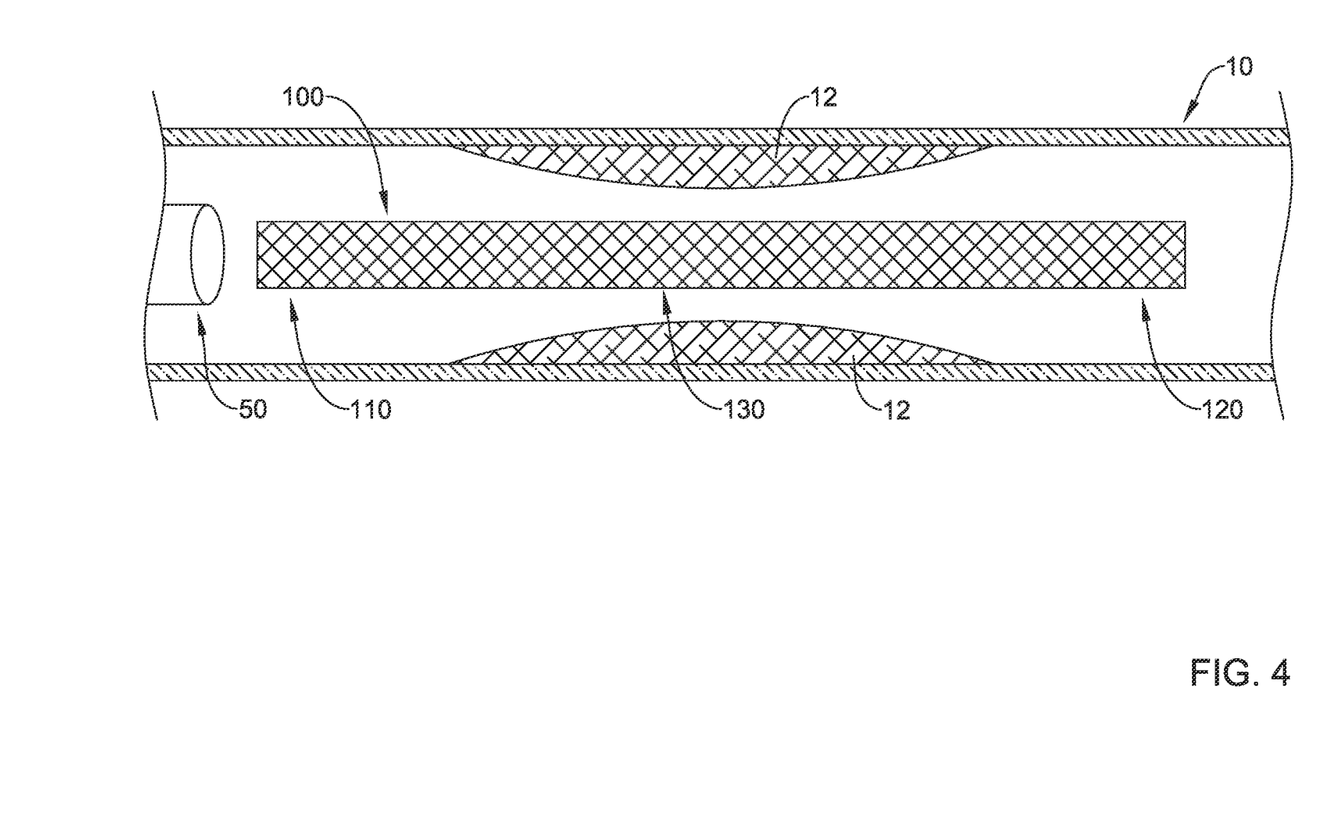
FIGS. 4 and 5 illustrate aspects of a method of treating a stricture in a body lumen.
Figure 5:
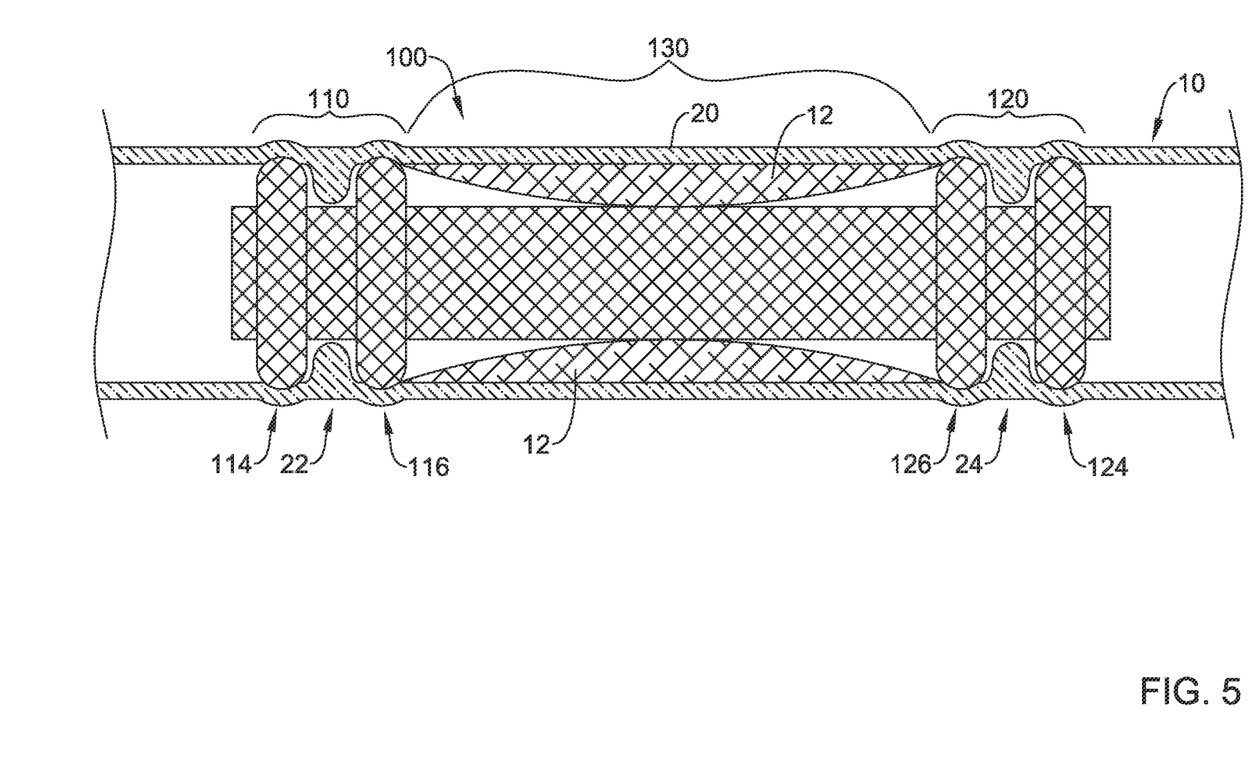

FIGS. 4 and 5 illustrate aspects of a method of treating a stricture 12 in a body lumen 10. The method is described herein with respect to the tubular body 100. However, the skilled artisan will recognize that the same method and/or steps may apply equally to the tubular body 200 and/or the tubular body 300, which elements may be used and/or applied interchangeably within the description provided.

In some embodiments, the method may include loading and/or positioning a stent including the tubular body 100 within a delivery catheter 50 in a delivery configuration. The delivery configuration may be and/or include an elongated and/or radially compressed configuration of the tubular body 100.

In some embodiments, the method may include positioning the stent within the body lumen 10 in the delivery configuration using the delivery catheter 50, wherein the stent is positioned with the saddle portion 130 of the stent spanning the stricture 12, the first flange portion 110 proximal of the stricture 12, and the second flange portion 120 distal of the stricture 12, as seen in FIG. 4 for example. The method may further include retracting and/or withdrawing the delivery catheter 50 from the stricture 12 and/or the body lumen 10 to release the stent and/or the tubular body 100 in the delivery configuration at the stricture 12.

In some embodiments, the method may include shifting the stent and/or the tubular body 100 from the delivery configuration to the deployed configuration. The deployed configuration may be and/or include a longitudinally shortened and/or radially expanded configuration of the tubular body 100. In some embodiments, in the deployed configuration, the first flange portion 110 may have a first radial outer extent greater than an outer radial extent of the saddle portion 130. In some embodiments, in the deployed configuration, the second flange portion 120 may have a second radial outer extent greater than an outer radial extent of the saddle portion 130. In at least some embodiments, in the deployed configuration, the saddle portion 130 may span an entire longitudinal length of the stricture 12.

As may be seen in FIG. 5 for example, in some embodiments, in the deployed configuration, a first flange 114 of the first flange portion 110 and a second flange 116 of the first flange portion 110 longitudinally spaced apart from the first flange 114 may capture a first portion 22 of a wall 20 of the body lumen 10 therebetween to anchor the stent and/or the tubular body 100 adjacent the stricture 12. In some embodiments, the first portion 22 of the wall 20 of the body lumen 10 may form a substantially annular structure extending radially inward from the wall 20 when captured between the first flange 114 and the second flange 116. In some embodiments, the wall 20 may be deflected radially outward by the first flange 114 and/or the second flange 116 in the deployed configuration.

In addition or alternatively, in some embodiments, in the deployed configuration, a third flange 124 of the second flange portion 120 and a fourth flange 126 of the second flange portion 120 longitudinally spaced apart from the third flange 124 may capture a second portion 24 of the wall 20 of the body lumen 10 therebetween to anchor the stent and/or the tubular body 100 adjacent the stricture 12. In some embodiments, the second portion 24 of the wall 20 of the body lumen 10 may form a substantially annular structure extending radially inward from the wall 20 when captured between the third flange 124 and the fourth flange 126. In some embodiments, the wall 20 may be deflected radially outward by the third flange 124 and the fourth flange 126 in the deployed configuration.

The materials that can be used for the various components of the stent 100/200/300 and the various elements thereof disclosed herein may include those commonly associated with medical devices. For simplicity purposes, the following discussion makes reference to the stent 100/200/300. However, this is not intended to limit the devices and methods described herein, as the discussion may be applied to other elements, members, components, or devices disclosed herein, such as, but not limited to, the expandable framework, the first flange portion, the second flange portion, the saddle portion, the polymeric cover, and/or elements or components thereof.

In some embodiments, the stent 100/200/300, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the stent 100/200/300, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the stent 100/200/300 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stent 100/200/300 to achieve the same result.

In some embodiments, a degree of Magnetic Resonance Imaging (MRI) compatibility is imparted into the stent 100/200/300 and/or other elements disclosed herein. For example, the stent 100/200/300, and/or components or portions thereof, may be made of a material that does not substantially distort the image and create substantial artifacts (i.e., gaps in the image). Certain ferromagnetic materials, for example, may not be suitable because they may create artifacts in an MRI image. The stent 100/200/300, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others. In some embodiments, the stent 100/200/300 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the stent 100/200/300 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the stent 100/200/300 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of treating a stricture in a body lumen, comprising:
   inserting a stent into the body lumen in a compressed delivery configuration, the stent including a tubular body having a proximal end, a distal end, and a middle portion therebetween, wherein when in the compressed delivery configuration, the tubular body has an elongated, radially compressed configuration;
   positioning the stent within the body lumen such that the middle portion spans the stricture while the proximal end is in the body lumen proximal of the stricture and the distal end is in the body lumen distal of the stricture;
   expanding an entire length of the stent to a deployed configuration within the body lumen, wherein when in the deployed configuration, the tubular body expands radially, with first and second spaced apart flanges radially extending adjacent the proximal end, wherein the first and second flanges extend radially outward beyond the middle portion; and
   capturing a first annular portion of a wall of the body lumen between the first and second flanges, the first annular portion of the wall extending radially inward from the wall between the first and second flanges, thereby anchoring the stent across the stricture.

2. The method of claim 1, wherein when the tubular body expands radially, third and fourth spaced apart flanges radially extend adjacent the distal end, wherein the third and fourth flanges extend radially outward beyond the middle portion and capture a second portion of the wall of the body lumen therebetween.

3. The method of claim 2, wherein the wall of the body lumen is deflected radially outward by at least some of the first, second, third, and fourth flanges.

4. The method of claim 2, wherein the second portion of the wall of the body lumen forms a substantially annular structure extending radially inward from the wall.

5. The method of claim 2, wherein at least a portion of the tubular body extends proximal of the first and second flanges, and at least a portion of the tubular body extends distal of the third and fourth flanges.

6. The method of claim 2, wherein when in the deployed configuration, the first and second flanges resist a first radial inward force, the third and fourth flanges resist a second radial inward force, and the middle portion resists a third radial inward force less than the first radial inward force and the second radial inward force.

7. The method of claim 1, wherein when in the deployed configuration, the middle portion spans an entire longitudinal length of the stricture.

8. The method of claim 1, wherein when in the compressed delivery configuration, an entirety of the tubular body has a substantially uniform outer diameter.

9. The method of claim 1, wherein the first and second flanges are formed monolithically with the middle portion.

10. The method of claim 1, wherein the first and second flanges are coaxial with the middle portion.

11. The method of claim 1, wherein the first and second flanges extend transverse to a central longitudinal axis of the tubular body.

12. The method of claim 1, wherein a longitudinal length of the middle portion is at least 50% of an overall longitudinal length of the tubular body.

13. The method of claim 1, wherein at least a portion of the tubular body includes a cover member.

14. A method of treating a stricture in a body lumen, comprising:
  inserting a stent into the body lumen in a delivery configuration, the stent including a tubular body having a proximal end, a distal end, and a middle portion therebetween, wherein when in the delivery configuration, the tubular body has an elongated, radially compressed configuration;
  positioning the stent exclusively within the body lumen such that the middle portion spans the stricture, the proximal end is positioned proximal of the stricture and the distal end is positioned distal of the stricture;
  expanding the stent to a radially expanded deployed configuration, wherein expanding the stent forms first and second longitudinally spaced apart flanges adjacent the proximal end, and third and fourth longitudinally spaced apart flanges adjacent the distal end;
  capturing a first annular portion of a wall of the body lumen between the first and second flanges, and capturing a second annular portion of the wall between the third and fourth flanges, the first annular portion of the wall extending radially inward from the wall between the first and second flanges and the second annular portion of the wall extending radially inward from the wall between the third and fourth flanges, thereby anchoring the stent across the stricture.

15. The method of claim 14, wherein the first, second, third, and fourth flanges extend radially outward beyond the middle portion.

16. The method of claim 14, wherein the body lumen is a patient's esophagus.

17. The method of claim 14, wherein the wall of the body lumen is deflected radially outward by at least some of the first, second, third, and fourth flanges.

18. A method of treating a stricture in a body lumen, comprising:
  inserting a stent into the body lumen in a delivery configuration, the stent including a tubular body having a proximal end, a distal end, and a middle region therebetween, wherein when in the delivery configuration, the tubular body has an elongated, radially compressed configuration;
  positioning the stent within the body lumen such that the middle region spans spanning the stricture while the proximal end is in the body lumen proximal of the stricture and the distal end is in the body lumen distal of the stricture;
  expanding the stent to a radially expanded deployed configuration with an entire length of the tubular body positioned within the body lumen, wherein in the radially expanded configuration the stent includes first and second longitudinally spaced apart flanges adjacent the proximal end, and third and fourth longitudinally spaced apart flanges adjacent the distal end, wherein the first and second flanges are radially expanded against the body lumen proximal of the stricture, and the third and fourth flanges are radially expanded against the body lumen distal of the stricture; and
  capturing a first annular portion of a wall of the body lumen between the first and second flanges, and capturing a second annular portion of the wall between the third and fourth flanges, the first annular portion of the wall extending radially inward from the wall between the first and second flanges and the second annular portion of the wall extending radially inward from the wall between the third and fourth flanges, thereby anchoring the stent across the stricture, wherein the first portion of the wall of the body lumen forms a substantially annular structure extending radially inward from the wall.

* * * * *